United States Patent [19]
Markart

[11] Patent Number: 6,151,110
[45] Date of Patent: Nov. 21, 2000

[54] MEASURING DEVICE FOR DETERMINING THE CONCENTRATION OF A SUBSTANCE IN A LIQUID

[75] Inventor: Ernst Markart, Munich, Germany

[73] Assignee: LRE Technology Partner GmbH, Munich, Germany

[21] Appl. No.: 09/158,870

[22] Filed: Sep. 23, 1998

[30]     Foreign Application Priority Data

Mar. 17, 1998 [DE] Germany .......................... 198 11 622

[51] Int. Cl.[7] .................................................. G01N 21/01
[52] U.S. Cl. ............................................................ 356/244
[58] Field of Search .................................... 356/244, 246, 356/446

[56]          References Cited

U.S. PATENT DOCUMENTS 4,968,140  11/1990  Berner et al. ........................... 356/244
5,993,746  11/1999  Priha et al. .............................. 356/244

*Primary Examiner*—Frank G. Font
*Assistant Examiner*—Amanda Merlino
*Attorney, Agent, or Firm*—McCormick, Paulding & Huber LLP

[57]          ABSTRACT

A measuring device for measuring the concentration of a substance in a liquid, especially a body liquid, is designed for use with a test card having test sections with test fields located next to one another in the longitudinal direction of the card. The device has a housing for receiving one or more test cards and has an exposed test card support surface providing a measuring station with a measuring opening through which optical or electrical sensors sense the test field of a test section of a test card. A hand actuatable transport mechanism, which may be an actuating lever, a transport roll or a transport belt is engageable with a test card in the housing to advance it forwardly to bring a test section to the measuring station. The housing for the device is made of upper and lower portions which may be movable relative to one another with that movement used to drive the transport mechanism. The device also includes a hand operable apparatus for cutting a used test section from the test card and various means are provided for inhibiting the test fields of the cards contained in the housing from coming into contact with ambient air in order to prevent the moisture and/or other factors in the ambient air from negatively influencing the usefulness of the test sections.

45 Claims, 5 Drawing Sheets

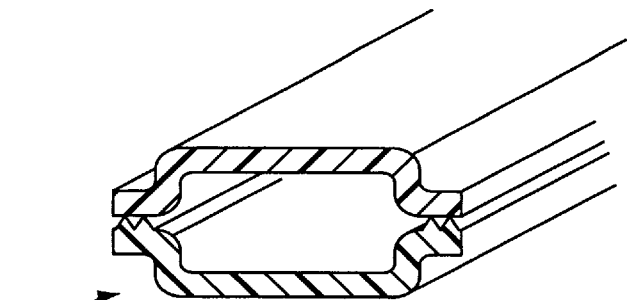
FIG. 7
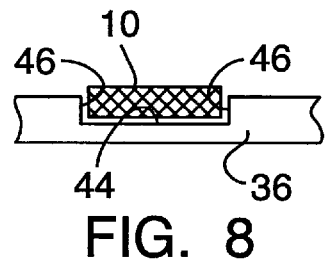
FIG. 8
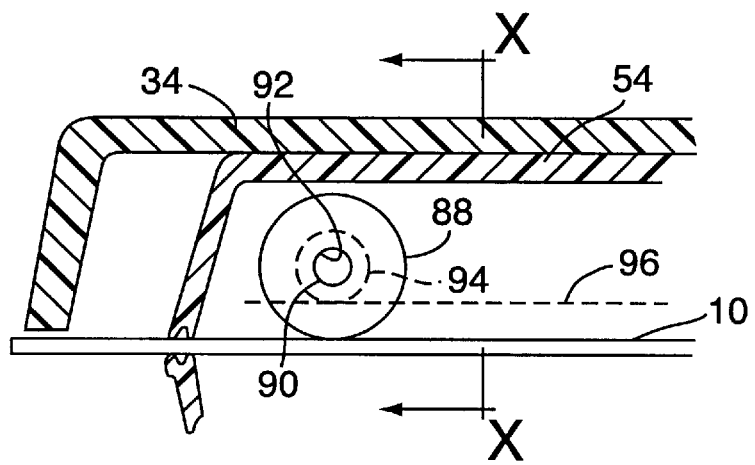
FIG. 9
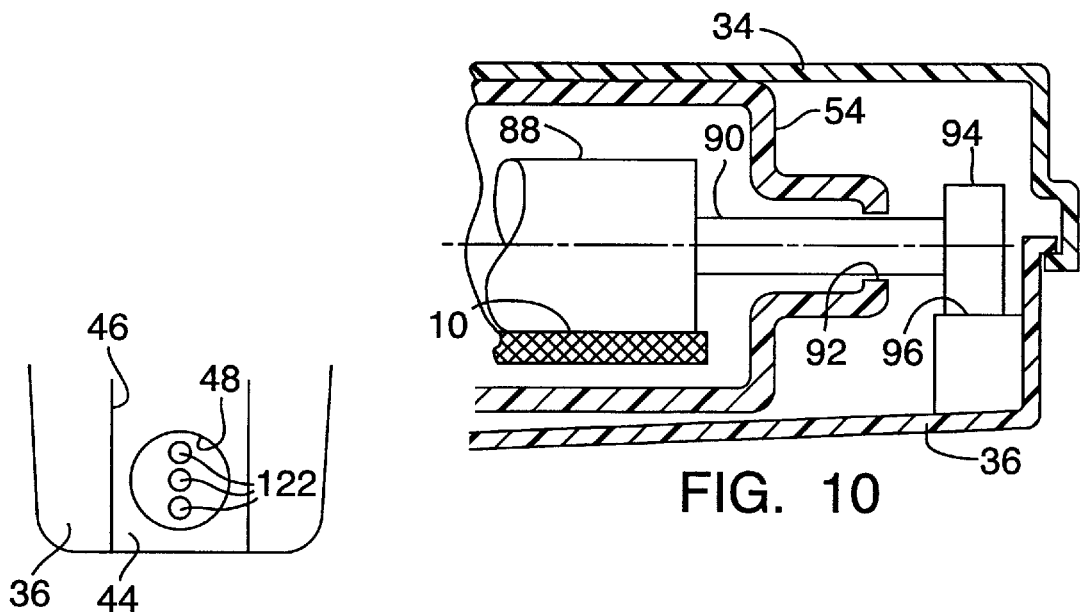
FIG. 15
FIG. 10

MEASURING DEVICE FOR DETERMINING THE CONCENTRATION OF A SUBSTANCE IN A LIQUID

FIELD OF THE INVENTION

The invention concerns a measuring device for determining the concentration of a substance in a liquid, especially a body liquid, by optical or electrical measurement of a test field provided on a test card, onto which test field the liquid to be investigated is applied, including a housing containing a receiving space for at least one test card, the housing having a housing upper portion and a housing lower portion. In the area of the plane separating the housing portions a test card support surface with a measuring station is formed, and the device also includes a measuring arrangement arranged in the area of the measuring station for measuring the test field, an evaluation and control device, and an indicating device.

BACKGROUND OF THE INVENTION

In not advance published German patent application 197 14 674, a measuring device of the above-mentioned type is described, in which a test card including several test strips can be inserted. The test card is located in a sleeve, from which it can be pulled out so far that a test strip becomes exposed, so that the liquid to be investigated can be applied to the test field. For this purpose, the device has to be opened, to allow the operating person to grasp the test card and pull it from the sleeve.

SUMMARY OF THE INVENTION

The invention has as its object the provision of a measuring device of the previously mentioned type which is so formed that a test field containing section of the test card can be pushed forward in a simple way from the receiving space to the measuring station.

This object is solved in accordance with the invention in that both housing portions are slidable back and forth relative to one another over a predetermined range and in that a transport element is coupled with one of the housing portions, which transport element is intended to come into engagement with a test card, located in the receiving space and having at least one test section with a test field, in order to move the test card to the measuring station and to fix it at the measuring station in response to the relative shifting of the two housing portions.

The measuring device of the invention is exceptionally simple to operate and permits an automatic precise positioning of the test field at the measuring station.

In order to move the test card forwardly by one test section in a single step, it is advantageous if the predetermined shifting range corresponds to the extent of a test section measured parallel to the shifting movement.

In a very simple embodiment of the inventive solution, the transport element is an engaging piece adapted to be received in a transport recess in the test card. The engaging piece can, for example, be a pawl movable between an inserted position and a free position and biased towards its inserted position, so that the pawl during the advancing or transport stroke of the reciprocating motion becomes inserted into the transport recess, while during the rearward stroke of the reciprocating movement of the housing portions, it slides on and along the test card.

In another embodiment, the engaging piece is formed as a saw-toothed shaped feed dog which takes with it the test card during the forward reciprocation stroke while during the rearward reciprocating stroke, it slides over the test card. To avoid that during the rearward stroke the test card is not again shifted rearwardly by friction, the feed dog can be arranged in one housing portion, for example the upper housing portion, while a saw-toothed shaped stop dog is arranged on the other housing portion, for example the lower housing portion, with the inclined surface facing opposite to the transport direction. This stop dog during rearward movement of the feed dog enters into a transport recess of the test card and thereby keeps the test card from moving with the feed dog during the rearward movement of the feed dog.

On one hand to assure reception of the feed dog or of the stop dog into an associated transport recess of the test card, and on the other hand to facilitate the sliding of the test card over the inclined surface of the feed dog and/or of the stop dog, it is practical if the feed dog and/or the stop dog are elastically displaceable perpendicularly to the transport plane.

In a further embodiment of the invention, the transport element is formed by a transport roll designed to be supported on the test card, which transport roll is supported in one of the housing portions and is drivable by the other of the two housing portions during their relative shifting. The transport roll can move the test card by its frictional connection with the test card or also by positive engagement with the test card by being received in the transport recesses. In a preferred embodiment, the transport roll is coupled through a one-way clutch with a friction or gear wheel with which is associated a friction surface and/or a toothed track arranged on the other driving housing portion. This solution offers the possibility to make the shifting path of the two housing portions relative to one another independent of the extent in the advancing direction of the test section to be advanced, in that the diameter of the friction or gear wheel is different from, for example smaller than, the diameter of the transport roll.

An essential problem in measuring devices with a receiving space for the test card, which includes several test sections, is to assure that the not yet used test sections do not become changed. The reaction material used for the test fields is in general hydroscopic so that it will take up the liquid to be investigated as fast as possible and will react with it. This, however, leads to the fact that the reaction material takes on moisture from the ambient air so that in the case of long open storage of the test sections, the reaction behavior of the test fields can change in uncontrollable ways.

To make certain that in a given period of time the test card sections inside of the receiving space of the measuring device deliver similar measuring results under similar conditions within the framework of a permissible tolerance, in a preferred embodiment of the invention, the receiving space for at least one test card is formed by a container, which container is connected with one of the housing portions, while the transport element is connected with the other housing portion. Preferably the housing upper portion is connected with the container, so that an actuating lever coupled with the housing underportion extends into the container, which actuating lever carries the engaging piece and extends essentially parallel to the test card support surface. The test cards are, therefore, kept in a closed space which exchanges so little air with the surroundings that the humidity reaching the container can, for example, be neutralized by a drying medium in the test card so as to have little essential influence on the measuring accuracy. In a preferred embodiment, the container is an at least nearly rectangular closed hollow body which on its side facing the measuring station has a through going slot for the test card and on its opposite side, a through going opening for the actuating lever. The through going slot and the through going opening can, for example, each be bordered by a sealing lip so that even during the advancement of the test card through the through opening slot, practically no air can enter the inner space of the container. To make the container still more tightly sealed and to avoid the entry of air through the through opening for the actuating lever, the lever can be connected air tightly with the hollow body wall through which it passes. Since the actuating lever must, however, be movable relative to the container, this air-tight connection can, for example, be achieved by a bellows through which the lever passes and which seals the through going opening.

To simplify the manufacture of the container, this can consist of an elastic material so that it need not be made of several materials in combination.

To also assure in the case of a container suited for the reception of several test cards that the test card to be advanced comes into positive contact with the transport element, the support surface for the test card in the container can be formed by a pressure plate, which pressure plate is biased away from the bottom of the underportion in the direction toward the transport element.

The actuating lever can itself be formed as an elastic spring or can be supported for elastic displacement, in order on one hand to assure reliable insertion of the feed dog arranged on it into a transport recess of the test card and on the other hand to pull the dog slidingly over the test card during rearward movement.

The drive of a transport wheel arranged inside of the container is achieved in that the shaft to which the friction or gear wheel is connected passes through the container wall in a sealed condition.

The container can be made of one piece. To allow better for cleaning, it is, however, practical if the container consists of two half shells which, along their edges, stand in contact with one another or are connected through sealing surfaces formed on the edges.

To achieve a clean separation of a used test section from the remainder of the test card without further helping means, it is practical if the measuring device has a separating means for cutting off the used test section from the test card. The separating means can, for example, be a cutting element adjustable essentially perpendicularly to the test card support surface. This cutting element can be rigidly connected with one of the housing portions, with the housing portion and the test strip support surface being movable relative to one another perpendicularly to the test strip support surface. Another possibility is that the cutting element is adjustably supported on one of the housing portions. That cutting element or the two housing portions are in this case preferably movable oppositely to one another against spring pressure so that the cutting element and the housing portion which carries it automatically return to their output positions.

The movably supported cutting element can, however, also carry a cam follower which so stands in engagement with a cam path on the other housing portion that the cutting element during a relative shifting of the housing portions is moved in the direction toward the test card.

The cutting element can, to improve its effectiveness, have an associated counter cutting element arranged on the other side of the test card support surface. In order to fix the housing portions during a cutting procedure relative to one another in the shifting direction, a portion of the cutting element or a pin connected with one of the housing portions can insertingly engage the other housing portion so that during cutting, the cutting element cannot be displaced from the counter cutting element. If the test sections of the test card are separated from one another by perforations or tear lines, the separating means can also be formed as an expanding element intended for reception in a recess of the test card in order to separatingly remove the used test section at the involved predetermined breaking line.

Of the separating means is arranged outside of the housing near the through opening for the test card, the used test card after its separation can freely fall away. The user need touch the test strip no more. On the other hand, it can be advantageous if the automatic falling away of the used test section is initially hindered. In this case, the separating means can be arranged inside of the housing near the through opening with a clamping lip being provided in the vicinity of the through opening to hold fast the separated test section. In this way it is avoided that the separated test section falls unintentionally to the ground.

To facilitate the positioning of the test section at the measuring station and to avoid a skewed advancement of the test card, the test card support surface advantageously has side guides for the test card.

Preferably the measuring device has a reading mechanism for sensing information stored on the test card, which information, for example, can contain characteristic data for the test to be carried out or batch data concerning the manufacture of the test card.

The operation of the measuring device is especially simple if, by way of the relative movement of the housing portions, at the same time a main switch is actuatable by means of which, for example, the device is turned on.

To assure that the test card is pushed forwardly so far that the test section lies over the measuring station, the measuring device can include a position control sensor which captures the position of the test section of the test card relative to the measuring station.

Advantageously, the measuring station is formed in an area of the housing lower portion not covered by the housing upper portion, so that the test field of the immediately to be used test section is exposed for the dropping on of the liquid to be investigated.

To avoid that liquid from the test card immediately being used does not reach the still unused test section bordering the used test section, the measuring station can be separated from the remainder of the test card support surface by a seal intended for engagement with the test card. The seal can, for example, annularly surround a measuring opening of the measuring station. This has the further advantage that the seal shields against stray light which might disturb an optical measurement.

If the measuring arrangement is an optical sensing one, it can have a plurality of individual sensors arranged behind one another inside of the measuring opening in the transport direction of the test card. These individual sensors can be so connected with the evaluation and control circuits that a measuring signal is produced only if the difference of the signals of at least two individual sensors is smaller than a pre-given threshold value.

The arrangement can also be such that one of the sensors is directed toward an inner standard or a reference surface of the test card or of a test section and that a measuring signal is only produced if, in the case of an empty measurement, the difference between the signals of the sensors and the signal of the one of the sensors directed onto the empty test field does not exceed a pre-given threshold value.

To limit as far as possible the entrance of ambient air with its moisture to the test sections in the housing, the arrangement in the container can be such that at least one of the container walls parallel to the test card occludingly lies on the test card. Thereby the test fields of the test card are covered and protected against the ambient influences.

The invention further concerns a measuring device for determining the concentration of a substance in a liquid, especially a body liquid, by optical or electrical measurement of a standard test field onto which the liquid to be investigated is applied, including a housing containing a receiving space for at least one test card, on which housing a test card support surface with a measuring station is formed, a measuring arrangement arranged in the area of the measuring station for measuring the test field, an evaluation and control circuit, and an indicator device. The test card can in the case of this embodiment inventively be advanced in the direction towards the measuring station in that in the housing an actuating lever is adjustably supported with an actuating end extending outwardly from the housing through a housing opening, the section of the lever lying inside of the housing carrying a feed dog intended for reception in a transport recess in a test card located in the receiving space and including at least one test section with a test field. By adjustment of the actuating lever from one position to a second position, the test card can be pushed forwardly in the direction toward the measuring station.

To avoid that with the movement of the actuating lever more than one test card is advanced, the feed dog on the actuating lever preferably is so sized that its extent in the insertion direction is at a maximum the same as the thickness of a test section.

Advantageously, the actuating lever is biased to its first position so that it will automatically return to such position.

In order that the actuating lever is not disturbed so long as it is not used, the arrangement is such that when the actuating lever in its second position, at which its actuating end is located at least significantly inside of the housing, it can be releasably held in the second position. Advantageously, the actuating lever in this case is biased to its releasably held position, so that it cannot automatically be released.

In accordance with a further feature, the invention concerns also a measuring device for determining the concentration of a substance in a liquid, especially a body liquid, by optical or electrical measurement of a standard test field on a test card onto which the liquid to be investigated is applied, including a housing containing a receiving space for at least one test card, on which housing a test card support surface with a measuring station is formed, a measuring arrangement arranged in the region of the measuring station to measure the test field, an evaluation and control circuit, and an indicator device. In this embodiment, a transport roll is supported preferably in the housing for transport of the test card within the housing, which transport roll is intended to engage a test card located in the receiving space and having at least one test section with a test field, in order to move the test card in the direction toward the measuring station.

In contrast to the above described solution in which the transport roll is driven by a relative shifting of the two housing halves, in the preceding mentioned solution the transport roll can be connected with an actuating wheel which at least partially extends out of the housing so that it is rotatable from the outside. In this case, the transport roll is advantageously coupled with the actuating wheel through a one-way clutch so that the transport roll can be turned only in one direction, that is, in the direction for pushing out the test card from the device.

To avoid that the test card be unintentionally pushed too far out of the measuring device, and to facilitate the positioning of the involved test section over the measuring station, it is proposed in accordance with the invention that the rotational path of the transport roll or of the actuating wheel in the transport direction be limited to a given range of angular rotation which at most corresponds to the extent of the test section in the transport direction.

In a modified embodiment of the invention, an endless transport belt is stretched over the transport roll and another roll with its axis parallel to that of the transport roll with the belt being intended for superimposed engagement with the test card. In this way, the frictional engagement between the transport device and the test card is increased. At the same time, the transport belt can be so guided that it lies above the test fields of the test card and seals them against undesired ambient influences.

In all of the above described embodiments, the container can be formed as an exchangeable test card magazine which if desired can have a through opening for the container lever. A code can be printed onto the container with code containing a batch identification of the stored test cards.

BRIEF DESCRIPTION OF THE DRAWINGS

Further features and advantages of the invention will be apparent from the claims and from the following description which explains the exemplary embodiments in connection with the accompanying drawings. The drawings are:

FIG. 7 A transverse section through the receiving space alone along the line VII—VII in FIG. 5.

FIG. 8 A schematic transverse section through the test strip support surface perpendicular to the plane of that surface.

FIG. 9 A schematic partial longitudinal section through a measuring device comprising another embodiment of the invention in which the transport element is a transport roll.

FIG. 10 A schematic partial cross-sectional view through the measuring device according to FIG. 9 taken on the line X—X in FIG. 9.

FIG. 15 A schematic plan view of the measuring station of a measuring device comprising a further embodiment of the invention.

DETAILED DESCRIPTION OF THE PREFERRED EMBODIMENTS

Figure 1:
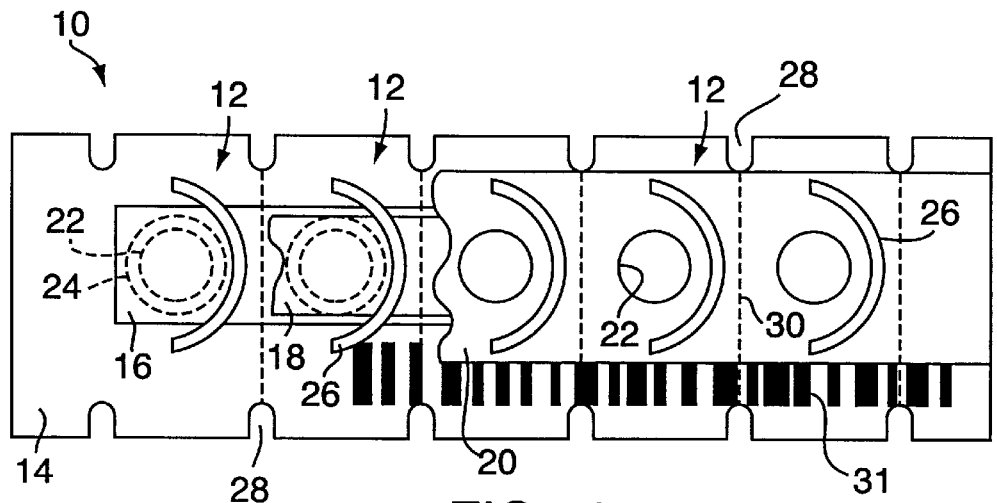
FIG. 1 A schematic plan view of a test card with several test sections and intended for use in a measuring device according to the invention.

FIG. 1 shows a test card, indicated generally at 10, in the form of an elongated strip with five test sections 12 arranged adjacent one another in the longitudinal direction of the strip.

The test card consists of a carrier layer or ply 14 on which are arranged in overlying relation to one another a reaction layer 16, a distributing layer 18 and a cover layer 20. In the middle of each test section 12, a circular application opening 22 is formed in the cover layer 20. Concentric with this, the carrier layer 14 has a measuring opening 24, the diameter of which is equal to or slightly greater than that of the drop application opening 22, as shown in FIG. 1.

If a drop of the liquid to be investigated is applied to the distribution layer 18 of the involved test section 12 through the drop application opening 22, the distribution layer 18 distributes the liquid uniformly over the underlying reaction layer. A reaction of certain chemicals with the substance, whose concentration in the applied liquid is to be determined, takes place in the reaction layer 16. This reaction leads to a color change which can be measured with the help of an optical sensing arrangement. The reaction can, however, also be so chosen that an electrochemical parameter is changed so that this change can be measured with the help of electrodes.

To inhibit an incursion of liquid from the just used test section to a subsequent not yet used test section 12, the reaction layer 16 and the distributing layer 18 of the individual test sections 12 are separated from one another by a gap or slit 26 which, for example, is of half circular shape and curved about the drop application opening in the formation of the test fields. In the illustrated exemplary embodiment, this gap 26 passes through the cover layer 20 and the carrier layer 14 and passes through and completely separates the less wide inner lying layers 16 and 18. This solution has the manufacturing advantage that the separating gaps 26 can be created by stamping after the joining of the, for example, four layers 14–20.

The test card 10 has recesses 28 regularly spaced from one another along its longitudinal edges, into which recesses still to be described transport elements of a measuring device can be received, in order to transport the test card mechanically in the measuring device. The two transport recesses 28 lying between individual test sections 12 are connected with one another by lines of perforation or other lines of weakening 30, which are provided in all of the layers 14–20 lying above one another, so that the individual test sections 12 can be easily and cleanly separated from one another. The separation can, however, also be accomplished with a cutting apparatus, which is explained in more detail hereafter.

In the case of the test card illustrated in FIG. 1, a bar code 31 is printed onto the edge area of the carrier layer 14 which extends outwardly beyond the cover layer 20. This bar code contains information about the test card and about the test to be carried out, especially characteristic data for the evaluation of the test reaction. This data can, therefore, be read into the measuring device by means of a reading device provided in the measuring device upon insertion of the test card into the measuring device, so that it is assured that the measuring device is supplied with the required data for the tests to be carried out with the test card in question. The bar code, however, represents only one possibility for the storing of such information.

Figure 2:
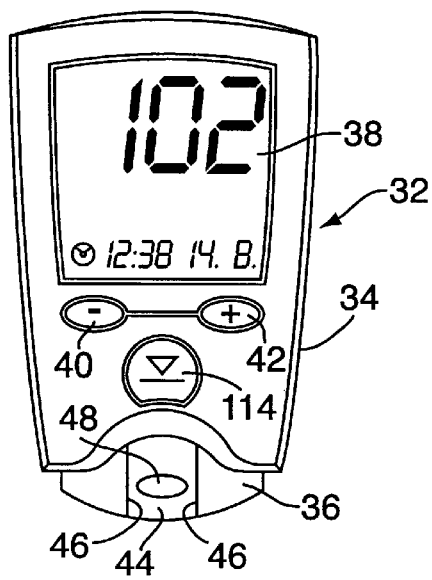
FIG. 2 A schematic view of a measuring device, without a test card, embodying the invention.

FIG. 2 shows an embodiment of a measuring device in accordance with the invention in schematic plan view. The measuring device includes a housing, indicated generally at 32, with a housing upper portion 34 and a housing lower portion 36. An indicating device is provided in the housing upper portion in the form of an LCD-screen 38. Further, operating elements 40, 42 for operating the device are provided.

Figure 5:
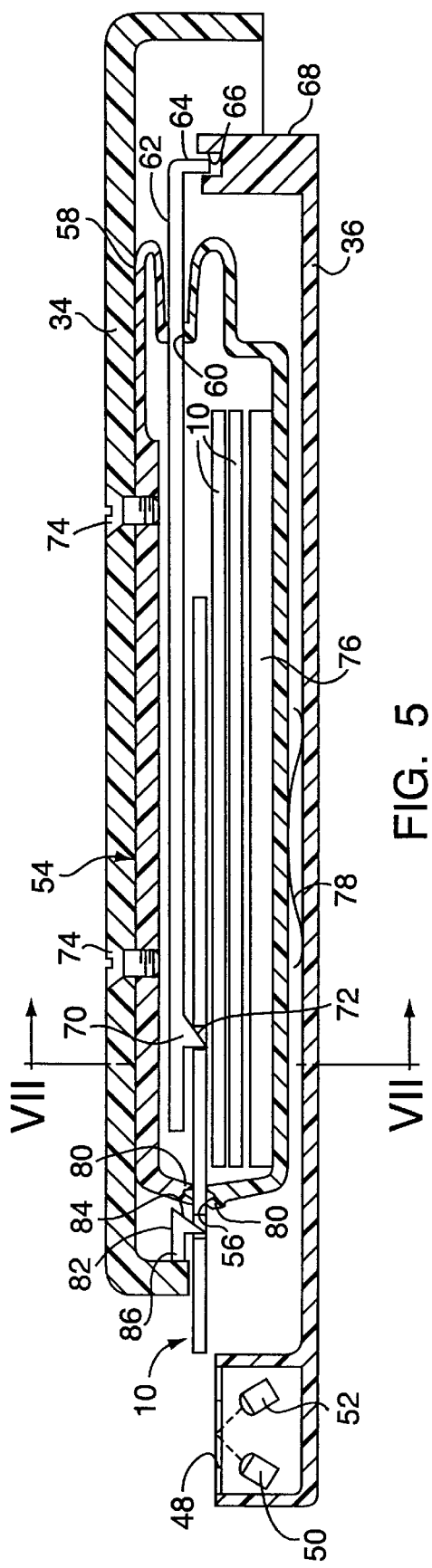
FIG. 5 A schematic longitudinal cross-section through a measuring device comprising another embodiment of the invention with its housing upper portion in its first position.
Figure 6:
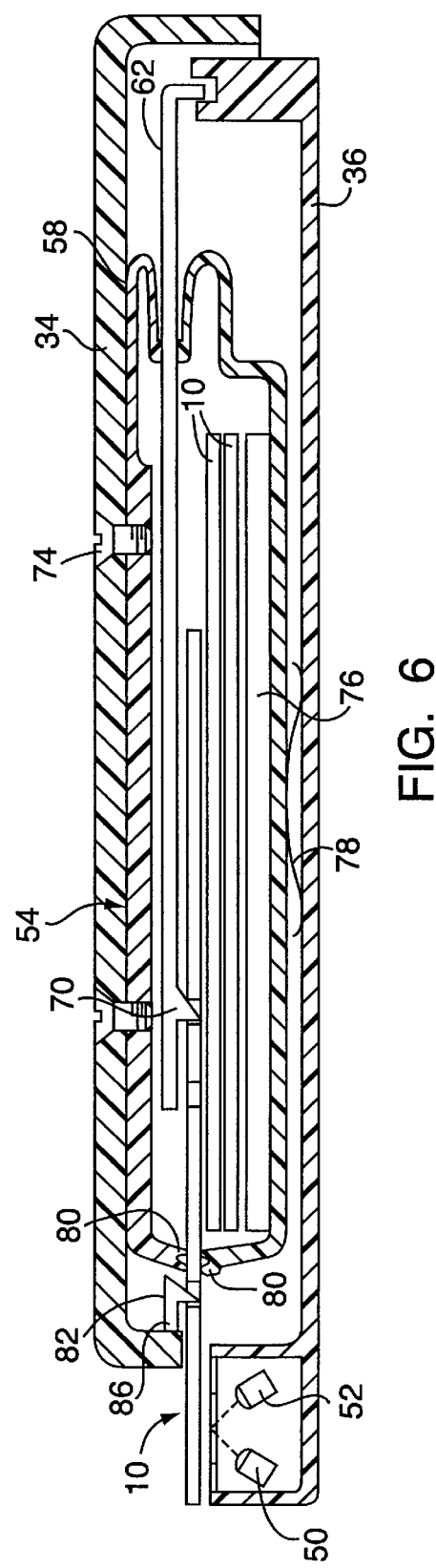
FIG. 6 A sectional view corresponding to FIG. 5 with the housing upper portion in its second position.

A test card support surface 44 for the test card 10 is formed in the housing lower portion 36. This test card support surface 44 has the form of a groove running in the longitudinal direction of the device by means of which the side walls 46 of the test card 10 is laterally guided. Near the forward end of the housing lower portion 36 and of the test card support surface 44 is a measuring station with a measuring opening 48. In the housing lower portion, as seen in FIGS. 5 and 6, an optical sensing arrangement with a light-emitting element 50 and a light-receiving element 52 is arranged below the measuring opening 48. The light emitted from the light-emitting element 50 is reflected at the test field of the involved test section 12 of the test card 10 and is received by the light-receiving element 52 which is connected with an evaluation and control circuit of the measuring device which is non-illustrated because of being known in itself.

Figure 3:
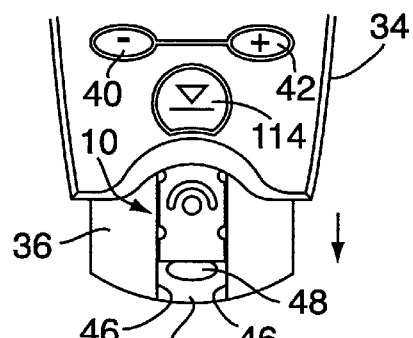
FIG. 3 A partial plan view of the measuring device of FIG. 2 with an inserted test card and with the housing upper portion of the measuring device in a first position.
Figure 4:
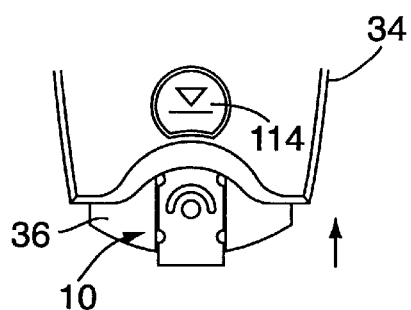
FIG. 4 A view corresponding to FIG. 3 of the measuring device with the upper portion of the measuring device in a second position.

As shown in FIGS. 3–6, the housing upper portion 34 and the housing lower portion 36 are shiftable parallel to one another in the longitudinal direction of the housing between a first position illustrated in FIGS. 3 and 5 and a second position illustrated in FIGS. 4 and 6. For one thing, by the shifting of the upper portion 34 relative to the lower portion 36 from the second position illustrated in FIGS. 4 and 6 to the first position illustrated in FIGS. 3 and 5, a non-illustrated main switch of the device can be actuated to turn on the device. For another thing, by repositioning the upper portion 34 to the FIGS. 4 and 6 illustrated second position, a test card 10 arranged in the measuring device is pushed forwardly onto the test card support surface 44 so that a test section 12 comes to lie over the measuring opening 48 of the measuring station of the housing lower portion 36, as shown by a comparison of FIGS. 3 and 4. The exact position of the involved test section 12 on the measuring station can be confirmed with the help of a non-illustrated position control sensor. The transport of the test card will now be explained in greater detail.

As shown in FIGS. 5 and 6, the housing 32 of the measuring device encloses a flat, nearly rectangular shaped container 54 for receiving a plurality of test cards 10. The container 54 consists of, for example, an elastic plastic and has at its front side turned toward the measuring station a slot shaped discharge opening 56 for a test card 10. At its rear or opposite side, it transitions into a bellows 58 having a pass through opening 60 for an actuating lever 62. This actuating lever has a bent end 64 turned away from the pass through opening 60 and hooked into a recess 66 in the rear wall 68 of the housing under portion 36. The actuating lever 62 has near its forward end closer to the pass through opening 56, a saw-toothed shaped feed dog 70 which with its inclined face 72 extends away from the pass through opening 56. The dog 70 is designed to be receivable in the recesses 28 of the test card 10. Advantageously two such dogs 70 are arranged in spaced relationship next to one another so that they are simultaneously receivable in a pair of transport recesses 28 along the longitudinal edges of the test card 10. As shown in FIGS. 5 and 6, the container 52 is fastened to the housing upper portion 34 by screws 74. A pressure plate 76 is arranged in the container 54 consisting of an elastic material, onto which pressure plate 76 the test card 10 lies. By means of a leaf spring 78 which, for example, is arranged between the bottom of the container 54 and the bottom of the housing lower portion 36, the container bottom and thereby the pressure plate 76 is urged upwardly against the actuating lever 62 so that the uppermost test card 10 is held in engagement with the feed dog 70.

If the housing upper portion 34 is shifted from the position illustrated in FIG. 6 to the right into the position illustrated in FIG. 5, it takes with it the container 54, since the container is fastened by the screws to the upper portion 34. The uppermost test card 10 can, therefore, not follow this movement since it is held immovable relative to the housing lower portion 36 by the dog 70. If the housing upper portion 38 is shifted from the position illustrated in FIG. 5 to the left to the position illustrated in FIG. 6, it will take with it the card 10 because of the clamping effect of the sealing edges 80 bordering the pass through opening 56 of the container 54. If the shifting path of the upper portion 34 relative to the lower portion 36 is of such a measurement that it corresponds to the measurement of a test section 12 in the longitudinal direction of the card, the test card 10 with a simple back and forth movement of the upper portion 34 relative to the lower portion 36 is pushed forwardly by one test section 12, that is, is pushed outwardly from the container 54.

If the clamping effect between the sealing edges 80 is not sufficient to pull the test card 10 over the inclined face 72 of the feed dog 70, a further stop dog 82 can be arranged on the upper portion 34, as indicated in FIG. 5. This stop dog 82 likewise has the shape of saw tooth with an inclined face 84 facing toward the rear housing ends. It is fastened by an elastically deflectable arm 86 to the forward wall of the housing upper portion 34. The stop dog 82 and the feed dog 70 assure that, with a simple back and forth movement of the upper portion 34 relative to the lower portion 36, the uppermost test card 10 is drawn outwardly from the container 54 step by step and indeed in such a way that in the illustrated FIG. 6 positions of the test housing upper portion 34 and housing lower portion 36 the test field of one test section 12 lies over the measuring opening 48 of the measuring station of the housing lower portion 36.

In the case of an electrical current measurement, the same mechanism is used. However, in both cases movements can be made for preparatorily positioning the test section and test field so that the test section lies over the device.

The container 54 can consist of two halves, as schematically illustrated in FIG. 7, with these halves, for example, being releasably connected with one another along their longitudinal edges, so that on one hand the two halves of the container 54 can be adjusted in common relative to the housing upper portion 34 and so that on the other hand the container 54 can be opened to clean the container or, as the case may be, to remove torn off portions of the card from the container.

FIGS. 9 and 10 show am embodiment in which the test cards 10 are pushed out from the container 54 by a transport roll 88. The transport roll 88 lies with frictional engagement on the uppermost card 10. The transport roll 88 is supported by a shaft 90 in a bearing opening 92 in a side wall of the container 54. The shaft 90 carries at its outer end a friction wheel 94 which lies on a drive track 96 of the housing lower portion 36. Between the friction wheel 94 and the transport roll 88 is provided a non-illustrated one-way coupling which assures that the transport roll is driven by the drive wheel 94 only during the rearward movement of the housing upper portion 34 from its FIG. 6 position to its FIG. 5 position, that is, in FIG. 9 is driven in the clockwise direction, and is not driven in the reverse movement of the housing upper portion from the FIG. 5 position to the FIG. 6 position. In FIGS. 9 and 10, one sees that the friction wheel 94 has a smaller diameter than the transport roll 88. This leads to the fact that the transport roll 88 rotates by its movement in the FIG. 9 clockwise direction with a higher tangential speed than that of the friction wheel 94. Since as previously stated, the friction wheel 94 runs without slipping on the friction track 96, the test card 10 is thereby pushed forwardly relative to the housing underportion 36, that is pushed outwardly from the container 54. If, on the other hand, the diameters of the drive wheel 94 and of the transport roll 88 were the same, the transport roll 88 would simply roll on the test card 10 without moving it. During the oppositely directed movement, the transport roll 88 rolls on the upper surface of the test card without translatably shifting it, since the drive connection between the friction wheel 94 and the transport roll 88 during this movement is disengaged, thereby allowing the tangential speeds of the transport roll and the drive wheel be the same despite the difference in their diameters.

Another possibility is that the transport roll 88 and its shaft 90 be supported in the housing lower portion 36 and that the drive track be provided in the housing upper portion 34. In this case the container 54 must have a slot in its upper portion 34 extending in the shifting direction for the passing through of the shaft 90.

Figure 11:
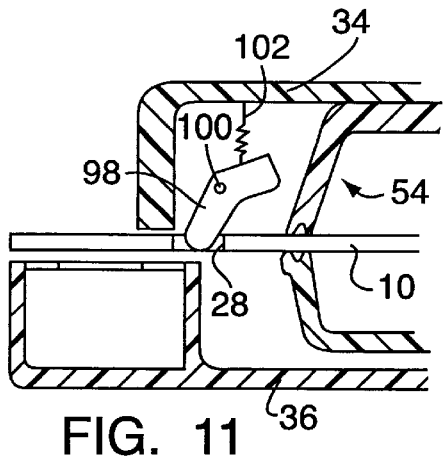
FIG. 11 A schematic longitudinal sectional view through a measuring device comprising a further embodiment of the invention.

FIG. 11 shows an embodiment which differs from the embodiment of FIGS. 5 and 6 in that the stop dog 82 is replaced by a movable pawl pivotally supported by the upper housing portion 34 for movement about an axis 100 and biased by a spring 102 to its inserted position, at which it with its one end insertably engages a transport recess 28 in the test card.

Figure 12:
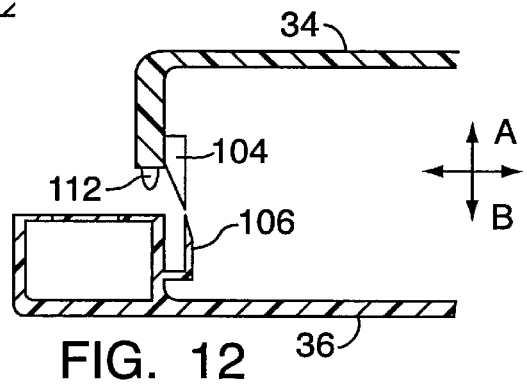
FIGS. 12–14 Are each a sectional view corresponding to FIG. 11 for explaining different embodiments of a separating device for separating a used test section from a test card.
Figure 13:
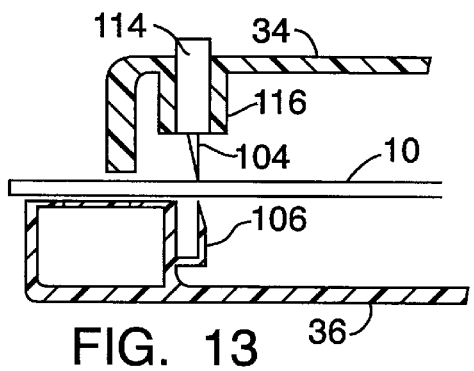
Figure 14:
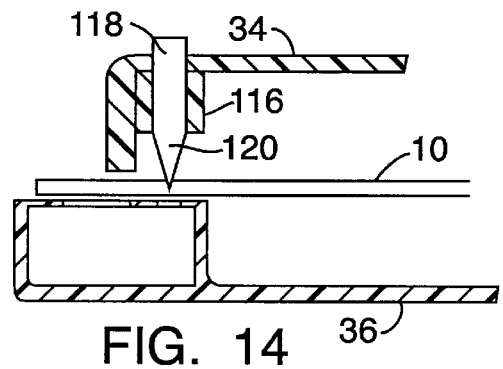

FIGS. 12–14 show different embodiments of a separating apparatus for cutting off a test section 12 from the test card 10. In the embodiment according to FIG. 12, a cutting blade 104 is arranged on the upper portion 34 for cooperation with a counterblade 106 on the housing lower portion 36. To move the two cutting elements 104 and 106 relative to one another, the two housing portions 34, 36 cannot only be shifted relative to one another in the direction of the double arrow A of FIG. 12 as has already been described, but they can also be moved toward one another against spring pressure in the direction of the arrow B. FIG. 10 shows an example of a guide for the movement of the two housing portions 34 and 36 relative to one another, which permits both a longitudinal shifting as well as a movement in the direction of the arrow B of the two portions relative to one another. In this guide, an outwardly directed rib 108 on a housing lower portion 36 is received with vertical play in a groove 110 formed in the housing upper portion and opening inwardly.

To avoid the cut off test section falling onto the ground, at least on one of the housing portions, in FIG. 12 the upper housing portion 34, in front of the separating apparatus 104, 106 has a clamping lip 112 which holds fast the cut off test section until the housing portions are let loose and the cut off test section freed.

FIG. 13 shows an embodiment in which the upper portion 34 and the lower portion 36 of the housing 32 are movable only in the direction of the arrow A relative to one another. In this embodiment, the upper cutting element 104 is fastened to a push key 114 which is movable in a guide 116 of the housing upper portion 34 perpendicularly to the test card support surface. The push key 114 is urged by a non-illustrated spring to its rest position so that the cutting effect can be obtained by a simple pressing onto the push key 114.

FIG. 14 shows a modified embodiment similar to the embodiment of FIG. 13 in which a push key 118 is slidably supported in the housing upper portion against spring pressure with the push key 118 at its end directed toward the test card support surface carrying a separating wedge 120. This wedge is designed to move into a slot shaped recess between two test sections and to separate the two neighboring test sections along a provided line of weakening, for example, a line of perforations.

In FIG. 15 is seen a measuring station with a measuring opening 48 in which three optical individual sensors 122 are arranged in a row parallel to the transport direction of the test card. The individual sensors are connected with the evaluation and control circuit so that a measuring signal is created only if the difference in the signals of at least two individual sensors exceed a pre-given threshold value. In this way, it can be assured that the involved test field lies essentially over the measuring opening 48 and that sufficient liquid has been applied to the test field.

Figure 16:
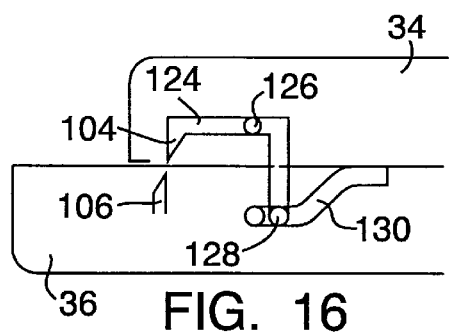
FIG. 16 A schematic representation of a positioning drive for the positioning of a cutting element for separating a test section from a test card.

FIG. 16 shows a special embodiment of the cutting element. The cutting element 104 is arranged on one end of a two armed lever 124 pivotally movable about an axis 126 fixed relative to one of the housing portions, for example, the upper housing portion 34. The cutting element 104 is designed for cooperation with a counter cutting element 106. The lever 124 at its end opposite to the cutting element 104 carries a cam follower in the form of a pin 128 which is received in a cam path or groove 130 formed in the other housing portion, for example, the lower housing portion 36. If the housing upper portion and housing lower portion are shifted relative to one another, as explained above, the pin 128 slides in the groove 130, whereupon the lever 124 is pivoted about its axis 126 so that the two cutting elements 104, 106 are moved to an away from one another.

Figure 17:
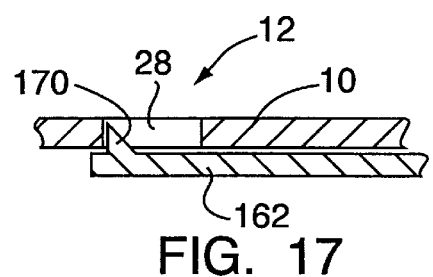
FIG. 17 A schematic section through a test card and the actuating lever in the area of a transport opening of the test card.

FIG. 17 shows a partial section through a test section 12 and an operating and transport lever 162 with a follower nose 170. It can be seen that the height of the follower nose 170 is smaller or equal to the thickness of the test section 12 so that the follower nose 170 which is received in the transport recess 28 cannot extend outwardly from the test section 12. In this way, it is assured that the nose 170 always engages and moves forwardly only one test card.

Figure 18:
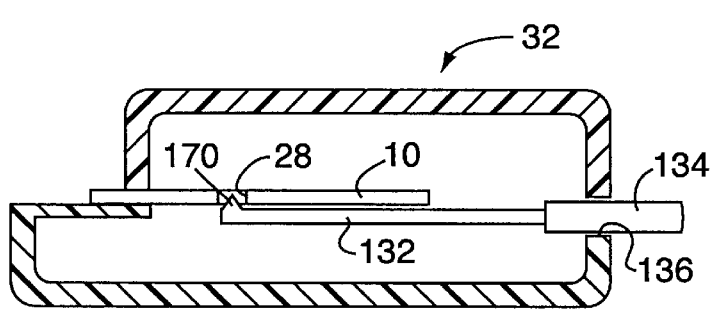
FIG. 18 A schematic section through the housing for receiving test cards with an actuatable transport lever extending outwardly therefrom.
Figure 19:
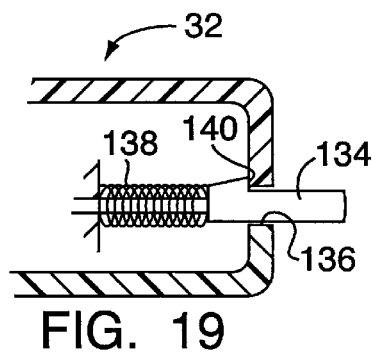
FIG. 19 A schematic partial section through the housing according to FIG. 18 for illustrating details at the transport end of the transport lever.

FIG. 18 shows in schematic way another embodiment of the inventive measuring device in which the test card 10 is pushed forwardly by an outwardly extending shiftable actuating or transport lever 132. The actuating lever 132 is supported in the housing 32 in a non-illustrated shiftable way and extends with its actuating end 134 out of the housing through an opening 136 in the housing 32. It has like the transport lever 162 a follower nose 170, designed for reception in a transport recess 28 of the test card 10. The actuating lever 132 is biased by a schematically illustrated spring 138 to its first position in which it with its actuating end 134 extends out of the housing 32 as illustrated in FIG. 18. By pressing onto the actuating end 134 against the force of the spring 138, the actuating lever 132 is pushed into the housing 32 and in doing this takes with it a test card 10 by way of the follower nose 170. The stroke of the actuating lever 132 can be of such measure that it corresponds to the length of a test section 12 in the transport direction or to a whole numbered fraction of such length. When the actuating lever 132 is not needed, it can be snap-fitted to the housing as shown in FIG. 19. That is, on the actuating end 134 of the lever, a stop leg 140 is formed by means of which the actuating lever 132 can be hooked onto the edge of the housing opening 136.

Figure 20:
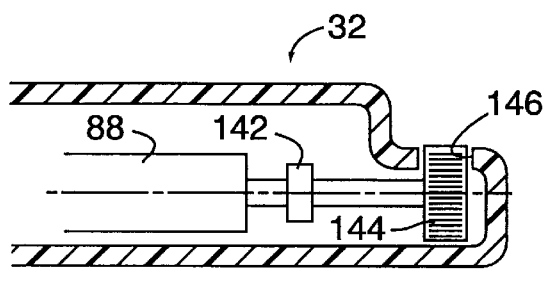
FIG. 20 A schematic partial transverse section through the housing in the area of the transport roll and through the actuating wheel connected with the transport roll.
Figure 21:
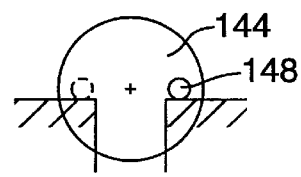
FIG. 21 A schematic end view of the actuating wheel in the axial direction for explaining the rotational angle limitation of the actuating wheel.

FIG. 20 shows in schematic way another type of drive for the transport roll illustrated in FIGS. 9 and 10. The transport roll 88 is connected through a one-way coupling 142 with an actuating wheel 144 which extends so far out of the housing 32 through an opening 146 that it can be turned by hand. The rotation of the actuating wheel and with it of the transport roll can be so limited by a stop 148 (FIG. 21) that the actuating wheel and with it the transport roll can be rotated only over a predetermined rotational angle which is of such measure that the transport stroke corresponds exactly to the measurement of a test section in the transport direction.

Figure 22:
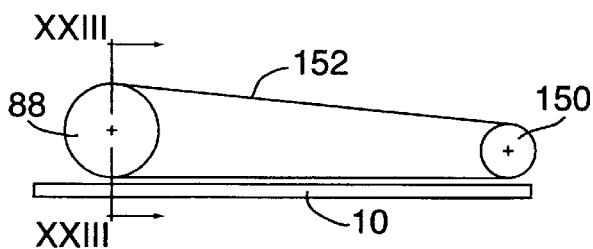
FIG. 22 A schematic side view of a modified form of a transport device for pushing forwardly the test cards inside of the housing.
Figure 23:
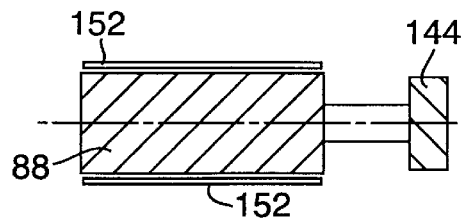
FIG. 23 A schematic transverse section through the transport device along the line XXIII—XXIII in FIG. 22.

FIGS. 22 and 23 show a modification of the transport apparatus wherein a transport belt 152 is tensioned over the transport roll 88 and a further roll 150 arranged with its axis parallel to that of the transport roll 88. The belt, for example, is made of rubber and lies flatly on the transport card to be transported and thereby covers the test fields of the test card. Thereby along with the transport function it, at the same time, provides a protection for the test fields against the effect of ambient moisture.

Figure 24:
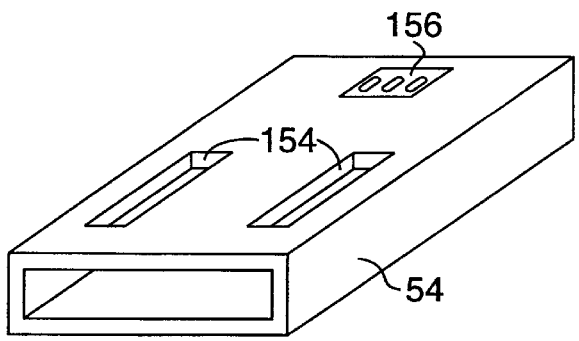
FIG. 24 A perspective schematic illustration of a container formed as a test card magazine, which is exchangeably insertable in the housing of the measuring device.

FIG. 24 shows an exchangeable container 54 formed as the test card magazine. For the embodiment according to FIG. 18, this test card holder has openings 154 through which a follower on the actuating lever 132 can be received in order to engage and move outwardly a test card in the transport magazine. The test cards can, therefore, in a way similar to that described in connection with FIGS. 5 and 6 be pressed by a spring-biased pressure plate or by a leaf spring alone against the upper side of the container 54 illustrated in FIG. 24 so that they can be engaged by the follower. On the outer side of the container is printed a code 156 which contains information about the test cards, their manufacturing data and their function.

What is claimed is:

1. A measuring device for determining the concentration of a substance in a liquid, especially a body liquid, by optical or electrical measurement of a test field provided on a test card (10), onto which the liquid to be investigated is applied, including a housing containing a space for receiving at least one test card (10) and having an upper housing portion (32)

and a lower housing portion (36), on which in the area of the separating plane of the housing (32) a test card support surface with a measuring station is formed, a measuring arrangement (50, 52) arranged in the area of the measuring station for measuring the test field, and evaluation and control apparatus, and an indicator (38), characterized in that both housing portions (34, 36) are movable back and forth relative to one another along a pre-given range and in that a transport element (82, 88) is coupled with one of the housing portions (34, 36), said transport element being engagable with a test card (10) located in the receiving space and having at least one test section (12) with a test field, in order to move the test card in the direction toward the measuring station in dependence on the relative shifting movement of the two housing portions (34, 36).

2. A measuring device according to claim 1, further characterized in that the pre-given shifting range corresponds to the extent of at least one test section (12) measured parallel to the shifting path.

3. A measuring device according to claim 1, characterized in that the transport element is an engaging piece (82; 98) formed for insertable engagement in a transport recess (28) in the test card (10).

4. A measuring device according to claim 3, further characterized in that the engaging piece is a pawl (98) which is movable between an inserted position and a free position and is biased to its inserted position.

5. A measuring device according to claim 3, further characterized in that the engaging piece is formed as a saw-toothed shape feed dog (82) whose inclined face (84) faces oppositely to the transport direction.

6. A measuring device according to claim 5, further characterized in that the feed dog (82) is arranged on the housing upper portion (34) and in that on the housing lower portion (36) is arranged a saw-toothed shape stop dog (70) whose inclined face (72) faces oppositely to the transport direction.

7. A measuring device according to claim 6, further characterized in that the feed dog (82) and/or the stop dog (70) is elastically deflectable perpendicularly to the transport plane.

8. A measuring device according to claim 1, further characterized in that the transport element is formed as a transport roll (88) for engagement with the test card (10), which roll is supported in one of the housing portions (34, 36) and is drivable by the other of said two housing portions during the relative shifting of said two housing portions.

9. A measuring device according to claim 8, further characterized in that the transport roll (88) is coupled by a one-way coupling with a friction or toothed wheel (94), and in that a friction surface (96) or a toothed track is arranged on said driving other one housing portion (36).

10. A measuring device according to claim 9, further characterized in that the diameter of the friction or toothed wheel (94) is different from the diameter of the transport roll (88).

11. A measuring device according to claim 1, further characterized in that the receiving space for the at least one test card (10) is formed by a container (54) connected with one of said housing portion (34, 36), with the transport element connected with the other housing portion (36, 34).

12. A measuring device according to claim 11, further characterized in that the container (54) is connected with the upper housing portion (36) and in that an actuating lever (62) is received in said container and coupled with the housing lower portion (36), which actuating lever carries an engaging piece (70) and extends generally parallel to the test card support surface (44).

13. A measuring device according to claim 12, further characterized in that the container (12) has an at least nearly rectangular closed hollow body shape and on its side facing the measuring station has a through slot (56) for the test card (10) and on its opposite side has a pass through opening (60) for the actuating lever (62).

14. A measuring device according to claim 13, further characterized in that the pass through slot (56) and the pass through opening (60) are bordered by sealing lips (80).

15. A measuring device according to claim 13, further characterized in that the lever (52) is air sealingly connected with the wall of said container through which it passes.

16. A measuring device according to claim 15, further characterized in that the pass through opening (60) is sealed by a bellow (58) through which the lever (62) passes.

17. A measuring device according to claim 12, characterized in that the actuating lever (62) is itself elastically deflectable or is supported for elastic deflection.

18. A measuring device according to claim 11, further characterized in that the transport element is formed as a transport roll for engagement with the test card (10), which transport roll is supported in one of the housing portions (34, 36) and is drivable by the other of the two housing portions (36, 34) by the relative shifting of the two housing portions, said transport roll being coupled by a one-way coupling with a friction or toothed wheel (94), in that a friction surface (96) or a toothed track is arranged on the driven other one of the housing portions (36) and in that a shaft (90) connecting the transport roll (88) with the friction or toothed wheel (98) sealingly passes through the wall of the container.

19. A measuring device according to claim 11, further characterized in that the container (54) is made of an elastic material.

20. A measuring device according to claim 19, further characterized in that at least one of the container walls which extends parallel to the test card lies sealingly on the test card (10).

21. A measuring device according to claim 11, further characterized in that the support surface for the test card (10) is formed by a pressure plate (76) in the container (54), which pressure plate is biased away from the bottom of the housing lower portion (36) in the direction toward the transport element (70; 88).

22. A measuring device according to claim 11, further characterized in that the container (54) consists of two half shells which shells have sealing surfaces formed along their edges which sealing surfaces stand in engagement with one another.

23. A measuring device according to claim 11, further characterized in that the container (54) is formed as one piece.

24. A measuring device according to claim 1, further characterized in that it has a separating mechanism (104, 106; 120) for separating a used test section 12 from a test card (10).

25. A measuring device according to claim 24, further characterized in that the separating apparatus has a movable cutting element (104) movable essentially perpendicularly to the test card support surface (44).

26. A measuring device according to claim 25, further characterized in that the cutting element (104) is rigidly connected with one of the housing portions (34, 36) and in that the housing portions (34, 36) are movable relative to one another perpendicularly to the test card support surface (44).

27. A measuring device according to claim 26, further characterized in that the housing portions (34, 36) are movable relative to one another against spring pressure.

28. A measuring device according to claim 25, further characterized in that the cutting element (104) is adjustably supported on said one housing portion (34, 36).

29. A measuring device according to claim 28, further characterized in that the movable cutting element (104) carries a tam (128) standing in contact with a tam path (130) formed on the other of said housing portions so that the cutting element (109) is moved essentially perpendicularly to the test card (10) in response to a relative shifting of the housing portion (34, 36).

30. A measuring device according to claim 24, further characterized in that a counter cutting element (106) is arranged on the other side of the test card support surface (44) for cooperation with said cutting element (104).

31. A measuring device according to claim 29, further characterized in that a portion of the cutting element or a pin connected with said one housing portion during a cutting procedure extends into the other housing portion to fix the two housing portions against movement relative to one another in the shifting direction.

32. A measuring device according to claim 24, further characterized in that the transport apparatus has a spreading element (120) designed for reception in a recess of the test card (20) to separate a used test section (12) at a predetermined break position (30).

33. A measuring device according to claim 24, further characterized in that the separating apparatus is arranged outside of the housing (32) near the pass-through opening (56) for the test card (10).

34. A measuring device according to claim 24, further characterized in that the separating apparatus is arranged inside of the housing (32) near the pass-through opening (56) and in that in the area of the pass-through opening a clamping lip (112) is provided for holding fast the separated test section (12).

35. A measuring device according to claim 1, further characterized in that the test card support surface (44) has side guides (46) for the test card (10).

36. A measuring device according to claim 1, further characterized in that it has a reading apparatus for sensing information stored on the test card (10).

37. A measuring device according to claim 1, further characterized in that it has a main switch which is actuatable by a relative movement of the housing portions (34, 36).

38. A measuring device according to claim 1, further characterized in that it has a position control sensor for capturing the position of a test section (12) of the test card relative to the measuring station.

39. A measuring device according to claim 1, further characterized in that the measuring station is formed in a region of the housing lower portion (36) not covered by the housing upper portion (34).

40. A measuring device according to claim 1, further characterized in that the receiving space is formed for receiving a plurality of test cards (10).

41. A measuring device according to claim 1, further characterized in that the measuring station is separated from the remainder of the test card support surface (44) by a seal designed to engage the test card (10).

42. A measuring device according to claim 41, further characterized in that the seal annularly surrounds a measuring opening (48) of the measuring station.

43. A measuring device according to claim 1, further characterized in that the measuring arrangement is an optical sensor arrangement having a plurality of individual sensors, which sensors are arranged in the measuring opening (48) behind one another in the transport direction of the test card (10).

44. A measuring device according to claim 43, further characterized in that the individual sensors are so connected with the evaluation and control circuit that a measuring signal is produced only if the difference of the signals of at least two individual sensors is smaller than a predetermined threshold value.

45. A measuring device according to claim 44, further characterized in that one of the sensors is directed toward an inner standard or a reference surface of the test card (10) or a test section (12) and that a measuring signal is only outputted if in the case of an empty measurement the difference between the signal of this sensor and the signal of one of the sensors directed to the empty test field does not exceed a pre-given threshold value.

* * * * *